US009043191B2

(12) United States Patent
Grady et al.

(10) Patent No.: US 9,043,191 B2
(45) Date of Patent: *May 26, 2015

(54) SYSTEMS AND METHODS FOR IDENTIFYING PERSONALIZED VASCULAR IMPLANTS FROM PATIENT-SPECIFIC ANATOMIC DATA

(71) Applicant: HeartFlow, Inc., Redwood City, CA (US)

(72) Inventors: Leo Grady, Millbrae, CA (US); Charles A. Taylor, San Mateo, CA (US); Gilwoo Choi, Mountain View, CA (US); Campbell Rogers, Portola Valley, CA (US)

(73) Assignee: HeartFlow, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/254,630

(22) Filed: Apr. 16, 2014

(65) Prior Publication Data
US 2015/0051886 A1 Feb. 19, 2015

Related U.S. Application Data

(60) Provisional application No. 61/866,758, filed on Aug. 16, 2013.

(51) Int. Cl.
G06G 7/48 (2006.01)
G06F 19/00 (2011.01)
G06F 17/50 (2006.01)

(52) U.S. Cl.
CPC ........ G06F 19/3437 (2013.01); G06F 17/5009 (2013.01)

(58) Field of Classification Search
CPC .................................................. G06F 17/5009
USPC ........................................................... 703/11
See application file for complete search history.

(56) References Cited

U.S. PATENT DOCUMENTS

2010/0017171 A1* 1/2010 Spilker et al. ..................... 703/2
2012/0041318 A1 2/2012 Taylor (Continued)

OTHER PUBLICATIONS

Spilker and Taylor (inventor): Tuning Multidomain Hemodynamic Simulations to Match Physiological Measurements; Annals of Biomedical Engineering, vol. 38, No. 8, Aug. 2010, pp. 2635-2648.*

(Continued)

Primary Examiner — Hugh Jones
(74) Attorney, Agent, or Firm — Bookoff McAndrews, PLLC

(57) ABSTRACT

Embodiments include methods of identifying a personalized cardiovascular device based on patient-specific geometrical information, the method comprising: generating a patient specific model of at least a portion of a patient's vasculature from image data of the patient's vasculature and one or more measured or estimated physiological or phenotypic parameters of the patient; determining pathology characteristics from cardiovascular geometry of the patient specific model; defining an objective function for a device based on design considerations and one or more estimates of hemodynamic and mechanical characteristics; optimizing the objective function, by simulating at least one change in devices and evaluating the objective function using fluid dynamic or structural mechanic analysis; and using the optimized objective function to either (i) select a device from a set of available devices or (ii) manufacture a desired device.

20 Claims, 2 Drawing Sheets

(56) References Cited

U.S. PATENT DOCUMENTS

2012/0041320 A1* 2/2012 Taylor ............................ 600/508
2012/0053918 A1* 3/2012 Taylor .............................. 703/9

OTHER PUBLICATIONS

Int Search Report PCT US 2013057546 Nov. 2013, 3 pages.*
Kim et al. (and inventor) Patient-Specific Modeling of Blood Flow and Pressure in Human Coronary Arteries; Annals of Biomedical Engineering, vol. 38, No. 10, Oct. 2010; pp. 3195-3209.*
Taylor et al. (inventor): Patient-Specific Modeling of Cardiovascular Mechanics; Ann. Rev. Biomed. Eng. 2009. 11:109-136.*
Tarun Chakravarty et al., *Meta-analysis of incidence, clinical characteristics and implications of stent fracture*, 106(8) Am J Cardiol. 1075-80 (2010).
Satjit Adlakha et al., *Stent fracture in the coronary and peripheral arteries*, 23(4) J Interv Cardiol. 411-19 (2010).
Timothy Canan and Michael S. Lee, *Drug-eluting stent fracture: incidence, contributing factors, and clinical implications*, 75(2) Catheter Cardiovasc Interv. 237-45 (2010).
Frank JH Gijsen et al., *Simulation of stent deployment in a realistic human coronary artery*, 7:23 Biomed Eng Online (2008) (11 pages).
Sanjay Pant et al., *Multiobjective design optimization of coronary stents*, 32(31) Biomaterials 7755-73 (2010).
Peter Mortier et al., *Virtual bench testing of new generation coronary stents*, 7(3) EuroIntervention 369-76 (2011).
Lucas H. Timmins et al., *Increased artery wall stress post-stenting leads to greater intimal thickening*, 91(6) Lab Invest. 955-67 (2011).
Sanjay Pant et al., *Geometry parameterization and multidisciplinary constrained optimization of coronary stents*, 11(1-2) Biomech Model Mechanobiol. 61-82 (2011).
Houman Zahedmanesh and Caitriona Lally, *Determination of the influence of stent strut thickness using the finite element method: implications for vascular injury and in-stent restenosis*, 47(4) Med Biol Eng Comput. 385-93 (2009).
Ian Pericevic et al., *The influence of plaque composition on underlying arterial wall stress during stent expansion: the case for lesion-specific stents*, 31(4) Med Eng Phys. 428-33 (2009).
Claudio Capelli et al., *Assessment of tissue prolapse after balloon-expandable stenting: influence of stent cell geometry*, 31(4) Med Eng Phys. 441-7 (2009).
Lucas H. Timmins et al., *Effects of stent design and atherosclerotic plaque composition on arterial wall biomechanics*, 15(6) J Endovasc Ther. 643-54 (2008).
E.W. Donnelly et al., *Finite element comparison of performance related characteristics of ballon expandable stents*, 10(2) Comput Methods Biomech Biomed Engin. 103-10 (2007).
Wei Wu et al., *Stent expansion in curved vessel and their interactions: a finite element analysis*, 40(11) J Biomech. 2580-5 (2007).
Julian Bedoya et al., *Effects of stent design parameters on normal artery wall mechanics*, 128(5) J Biomech Eng. 757-65 (2007).
C. Lally et al., *Cardiovascular stent design and vessel stresses: a finite element analysis*, 38(8) J Biomech. 1574-81 (2005); Erratum in: 39(9) J Biomech. 1760 (2006).
Francesco Migliavacca at al., *Stainless and shape memory alloy coronary stents: a computational study on the interaction with the vascular wall*, 2(4) Biomech Model Mechanobiol. 205-17 (2004).
P.J. Prendergast et al., *Analysis of prolapse in cardiovascular stents: a constitutive equation for vascular tissue and finite-element modeling*, 125(5) J Biomech Eng. 692-99 (2003).
Campbell Rogers et al., *Balloon-artery interactions during stent placement: a finite element analysis approach to pressure, compliance, and stent design as contributors to vascular injury*, 84(4) Circ Res. 378-83 (1999).
David Adalsteinsson and James A. Sethian, *A fast level set method for propagating interfaces*, 118(2) J. Comput. Phys. 269-277 (1995).
Elsa Angelini et al., *State-of-the-art of level set methods in segmentation and registration of medical imaging modalities*, Handbook of Biomedical Image Analysis—Registration Models, Kluwer Academic/Plenum Publishers, 47-102 (2005).
Thorsten Behrens et al., *Segmentation of tubular structures in 3D images using a combination of the Hough transform and a Kalman filter*, 2191 Proc. DAGM-Symp. Pattern Recognit. 406-413 (2001).
Fethallah Benmansour and Laurent D. Cohen, *A new interactive method for coronary arteries segmentation based on tubular anisotropy*, Proc. IEEE Int. Symp. Biomed. Imaging 41 (2009) (4 pages).
Yonatan Fridman et al., *Segmenting 3D branching tubular structures using cores*, Proc. Med. Image Comput. Assist. Interv. 570-577 (2003).
Yan Yang at al., *Knowledge-based 3D segmentation and reconstruction of coronary arteries using CT images*, Proc. IEEE Eng. Med. Biol. Soc. 1664-1666 (2004).
Jaeyoun Yi et al., *A locally adaptive region growing algorithm for vascular segmentation*, 13(4) Int. J. Imaging Syst. Technol. 208-214 (2003).
Francis K.H. Quek and Cemil Kirbas, *Vessel extraction in medical images by 3D wave propagation and traceback*, Proc. IEEE Symp. Biolnf. Bioeng., 174-181 (2003).
David Lesage et al., *A review of 3D vessel lumen segmentation techniques: models, features and extraction schemes*, 13(6) Med Image Anal. 819-45 (2009).
H.J. Kim et al., *Patient-specific modeling of blood flow and pressure in human coronary arteries*, 38(10) Ann Biomed Eng. 3195-209 (2010).
Charles A. Taylor, *Finite element modeling of blood flow in arteries*, 158(1) Comput Methods Appl Mech Eng. 155-96 (1998).
Andrea S. Les at al., *Quantification of hemodynamics in abdominal aortic aneurysms during rest and exercise using magnetic resonance imaging and computation fluid dynamics*, 38(4) Ann Biomed Eng. 1288-313 (2010).
Shawn C. Shadden and Charles A. Taylor, *Characterization of coherent structures in the cardiovascular system*, 36(7) Ann Biomed Eng. 1152-62 (2008).
C.A. Taylor and C.A. Figueroa, *Patient-specific modeling of cardiovascular mechanics*, 11 Annu Rev Biomed Eng. 109-34 (2009).
Pekkan, Kerem et al., "Patient-specific surgical planning and hemodynamic computational fluid dynamics optimizing through free-form haptic anatomy editing tool (SURGEM)", Aug. 5, 2008, 14 pages, vol. 46, No. 11, Medical & Biological Engineering & Computing, Springer, Berlin, Germany.
Griesbach et al., "Clinical Performance of Automatic Closed-Loop Stimulation Systems," Jul. 1, 2003, 6 pages, vol. 26, No. 7(p1), Pacing and Clinical Electrophysiology, Germany.
PCT International Search Report and Written Opinion, PCT/US2014/050030, filed Aug. 7, 2014, mailed Jan. 7, 2015, 12 pages.

* cited by examiner

SYSTEMS AND METHODS FOR IDENTIFYING PERSONALIZED VASCULAR IMPLANTS FROM PATIENT-SPECIFIC ANATOMIC DATA

PRIORITY

This application claims the benefit of priority from U.S. Provisional Application No. 61/866,758, filed Aug. 16, 2013, which is herein incorporated by reference in its entirety.

TECHNICAL FIELD

Various embodiments of the present disclosure relate generally to medical imaging and related methods. More specifically, particular embodiments of the present disclosure relate to systems and methods for identifying personalized vascular devices from patient-specific anatomic image data.

BACKGROUND

Coronary artery disease may produce coronary lesions in the blood vessels providing blood to the heart, such as a stenosis (abnormal narrowing of a blood vessel). As a result, blood flow to the heart may be restricted. A patient suffering from coronary artery disease may experience chest pain, referred to as chronic stable angina during physical exertion or unstable angina when the patient is at rest. A more severe manifestation of disease may lead to myocardial infarction, or heart attack.

Patients suffering from chest pain and/or exhibiting symptoms of coronary artery disease may be subjected to one or more tests that may provide some indirect evidence relating to coronary lesions. For example, noninvasive tests may include electrocardiograms, biomarker evaluation from blood tests, treadmill tests, echocardiography, single positron emission computed tomography (SPECT), and positron emission tomography (PET). Anatomic data may be obtained noninvasively using coronary computed tomographic angiography (CCTA). CCTA may be used for imaging of patients with chest pain and involves using computed tomography (CT) technology to image the heart and the coronary arteries following an intravenous infusion of a contrast agent.

Typically, cardiologists and other health care professionals analyze one or both of invasive tests and the above-described noninvasive tests to determine a suitable intervention for improving a patient's cardiovascular blood flow, when necessary. For example, a cardiologist may look at the images and, based on certain guidelines and know-how, select an intervention, such as a percutaneous coronary intervention (PCI) (i.e., a "stent") or coronary arterial bypass graft (CABG) to modify a patient's vasculature and blood flow. The design of medical implants is important for deliverability, long-term durability, and optimal treatment outcome for each patient. In the past, doctors and implant designers and manufacturers would evaluate the effectiveness of an implant design on an entire population of candidates for the implant, such as by using statistical analysis.

However, a need exists for a method for noninvasively assessing and predicting the effects of different interventions and implants on coronary anatomy, myocardial perfusion, and coronary artery flow of an individual patient. Such a method and system may benefit cardiologists who diagnose and plan treatments for patients with suspected coronary artery disease. In addition, a need exists for a method to predict coronary artery flow and myocardial perfusion under conditions that cannot be directly measured, e.g., exercise, and to predict outcomes of medical, interventional, and surgical treatments on coronary artery blood flow and myocardial perfusion of the individual patient. In addition, a need exists to automatically identify an optimal treatment option from a plurality of feasible treatment options (e.g., all possible PCI or CABG options), by analyzing noninvasively assessed coronary anatomy. Finally, a need exists for systems and methods for automatically designing, defining, or otherwise identifying a customized or personalized cardiac implant or other intervention for a specific patient, by analyzing noninvasively assessed coronary anatomy.

SUMMARY

According to certain aspects of the present disclosure, systems and methods are disclosed for identifying a personalized cardiovascular device based on patient-specific geometrical information. One method includes acquiring anatomical image data of at least part of the patient's vascular system; performing, using a processor, one or both of computational fluid dynamics and structural mechanics analysis on the anatomical image data; and identifying, using the processor, a personalized cardiovascular device for the patient, based on results of one or both of the computational fluid dynamics and structural mechanics analysis of the anatomical image data.

According to certain additional aspects of the present disclosure, one method of identifying a personalized cardiovascular device based on patient-specific geometrical information, includes: acquiring one or more physiological parameters of a patient, and anatomical image data of at least part of the patient's vascular system; performing, using a processor, one or both of computational fluid dynamics and structural mechanics analysis on the physiological parameters and anatomical image data; and identifying, using the processor, a personalized cardiovascular device for the patient, based on results of one or both of the computational fluid dynamics and structural mechanics analysis of the patient's physiological parameters and anatomical image data.

According to certain additional aspects of the present disclosure, one method of identifying a personalized cardiovascular device based on patient-specific geometrical information, includes: acquiring one or more physiological parameters of a patient, and a geometric model of at least a portion of the patient's vascular system; obtaining one or more geometric quantities of one or more coronary arteries of the geometric model of the patient's vascular system; determining the presence or absence of plaque at each of a plurality of locations in the geometric model of the patient's vascular system; generating an objective function defined by a plurality of device variables and a plurality of hemodynamic and solid mechanics characteristics; and optimizing the objective function using computational fluid dynamics and structural mechanics analysis to identify a plurality of device variables that result in desired hemodynamic and solid mechanics characteristics.

According to certain additional aspects of the present disclosure, one method of identifying a personalized cardiovascular device based on patient-specific geometrical information, includes: acquiring, in digital format, image data of a patient's vasculature, and one or more measured or estimated physiological or phenotypic parameters of the patient; generating a patient specific model of at least a portion of the patient's vasculature; determining pathology characteristics from cardiovascular geometry extracted from the patient specific model; defining an objective function for a device based on design considerations and one or more estimates of hemodynamic and mechanical characteristics; optimizing the objective function, by perturbing devices and evaluating the objective function using fluid dynamic or structural mechanic analyses; and using the optimized objective function to either (i) select a device from a set of available devices, or (ii) manufacture a desired device.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

Figure 1:
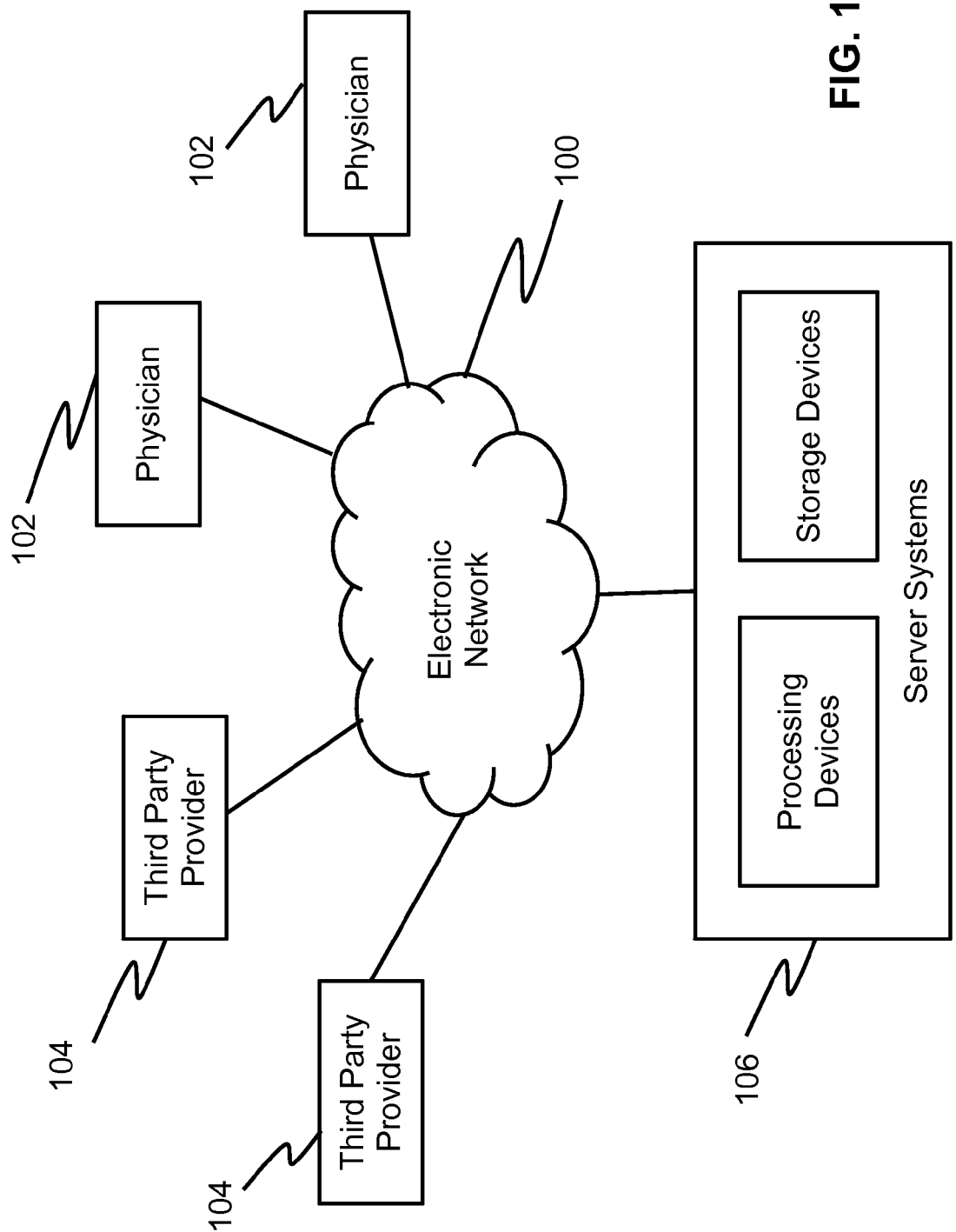
FIG. 1 is a block diagram of an exemplary system and network for designing personalized vascular implants from patient-specific anatomic image data, according to an exemplary embodiment of the present disclosure.

Reference will now be made in detail to the exemplary embodiments of the invention, examples of which are illustrated in the accompanying drawings. Wherever possible, the same reference numbers will be used throughout the drawings to refer to the same or like parts.

A new generation of noninvasive tests have been developed to assess blood flow characteristics. These noninvasive tests use patient imaging (such as CT) to determine a patient-specific geometric model of the blood vessels, which may be used computationally to simulate the blood flow using computational fluid dynamics (CFD) with appropriate physiological boundary conditions and parameters. Examples of inputs to these patient-specific boundary conditions include the patient's blood pressure, blood viscosity and the expected demand of blood from the supplied tissue (derived from scaling laws and a mass estimation of the supplied tissue from the patient imaging).

The present disclosure is directed to noninvasively assessing and predicting the effects of different interventions and implants on coronary anatomy, myocardial perfusion, and coronary artery flow of an individual patient. In addition, the present disclosure is directed to automatically identifying an optimal treatment option from a plurality of feasible treatment options (e.g., all possible PCI or CABG options), by analyzing noninvasively assessed coronary anatomy, and automatically designing, defining, or otherwise identifying a customized or personalized cardiac implant or other intervention for a specific patient, by analyzing noninvasively assessed coronary anatomy.

More specifically, the present disclosure is directed to an approach for providing a service for recommending and/or manufacturing personalized medical devices or delivery systems. Specifically, the presently disclosed systems and methods receive patient information (e.g., 3D medical imaging) and generate a patient-specific geometry of vessels and locations of pathologies for optimal device design. In one embodiment, the present disclosure includes a method of designing or identifying a personalized cardiovascular implant based on patient-specific geometrical information. The method involves acquiring one or more physiological parameters of a patient, and anatomical image data of at least part of the patient's vascular system; performing one or both of computational fluid dynamics and structural mechanics analyses on the physiological parameters and anatomical image data of a patient; and designing or identifying a personalized cardiovascular implant for the patient, based on results of one or both of the computational fluid dynamics and structural mechanics analysis of the patient's physiological parameters and anatomical image data. Although the present disclosure describes these systems and methods in the context of coronary artery disease, the same systems and methods are applicable for other vascular systems beyond the coronary arteries, such as peripheral or cerebral arteries or veins.

Referring now to the figures, FIG. 1 depicts a block diagram of an exemplary system and network for designing personalized vascular implants from patient-specific anatomic data. Specifically, FIG. 1 depicts a plurality of physicians 102 and third party providers 104, any of whom may be connected to an electronic network 100, such as the Internet, through one or more computers, servers, and/or handheld mobile devices. Physicians 102 and/or third party providers 104 may create or otherwise obtain images of one or more patients' cardiac and/or vascular systems. The physicians 102 and/or third party providers 104 may also obtain any combination of patient-specific information, such as age, medical history, blood pressure, blood viscosity, etc. Physicians 102 and/or third party providers 104 may transmit the cardiac/vascular images and/or patient-specific information to server systems 106 over the electronic network 100. Server systems 106 may include storage devices for storing images and data received from physicians 102 and/or third party providers 104. Server systems 106 may also include processing devices for processing images and data stored in the storage devices.

Figure 2:
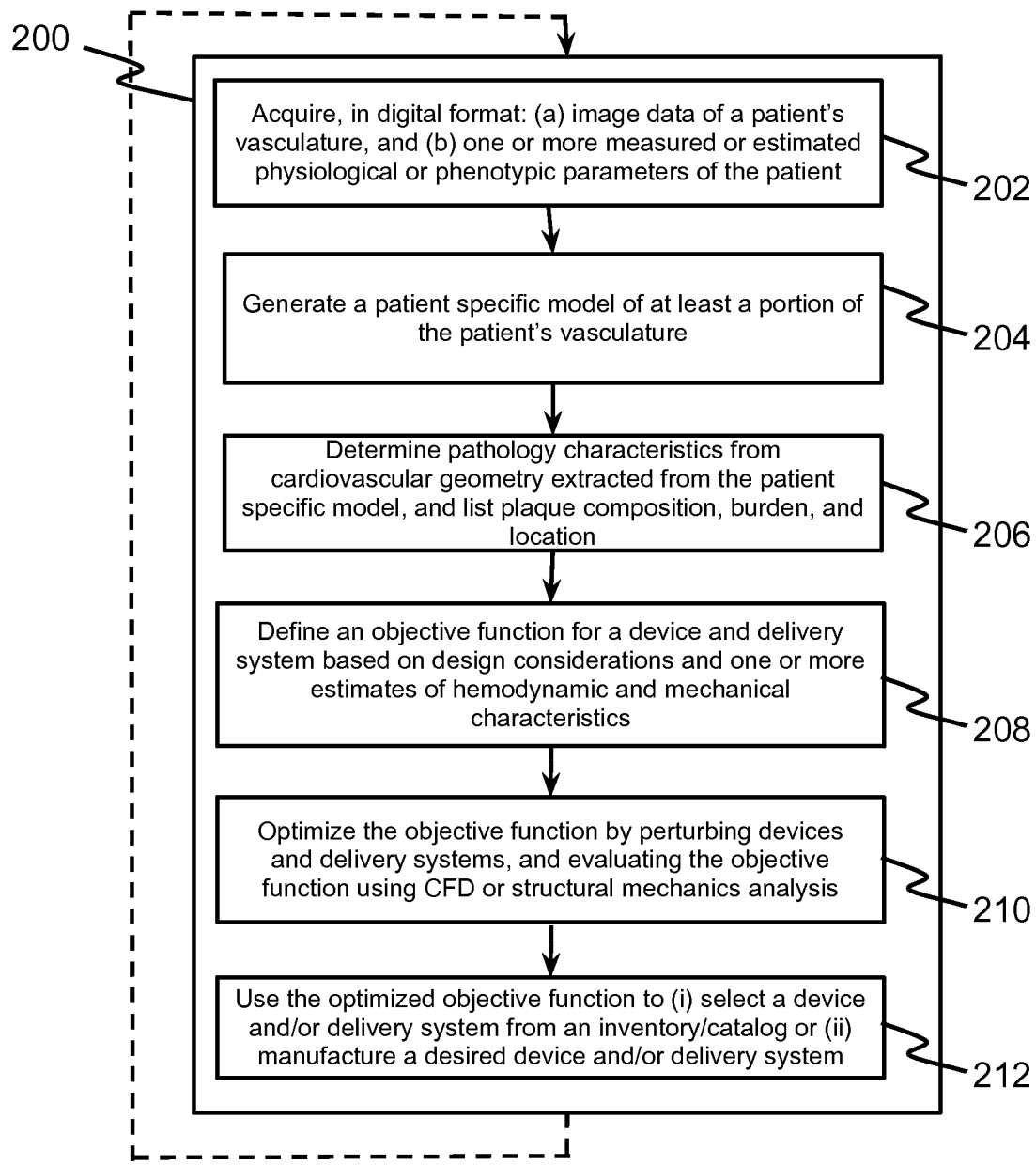
FIG. 2 is a block diagram of an exemplary method for designing personalized vascular implants from patient-specific anatomic image data, according to an exemplary embodiment of the present disclosure.

FIG. 2 is a block diagram of an exemplary method for designing personalized vascular implants from patient-specific anatomic data, according to an exemplary embodiment of the present disclosure. The method of FIG. 2 may be performed by server systems 106, based on information, images, and data received from physicians 102 and/or third party providers 104 over electronic network 100.

One embodiment of the present disclosure uses patients' cardiac imaging to derive a patient-specific geometric model of the coronary vessels and plaques, and perform computational fluid dynamics and structural mechanics analysis to determine the optimal design of medical implants or delivery systems. Specifically, as shown in FIG. 2, one method 200 for designing personalized vascular implants from patient-specific anatomic data may include obtaining image and patient information (step 202), such as by acquiring a digital representation (e.g., the memory or digital storage [e.g., hard drive, network drive] of a computational device such as a computer, laptop, DSP, server, etc.) of patient image data and a list of one or more estimates of physiological or phenotypic parameters of the patient, such as blood pressure, blood viscosity, patient age, patient gender, etc. Method 200 may further include generating a patient specific model of geometry of at least a portion of the patient's vasculature (step 204), such as for blood vessels, myocardium, aorta, valves, plaques, and/or cardiac chambers. This geometry may be represented as a list of points in space (possibly with a list of neighbors for each point) in which the space can be mapped to spatial units between points (e.g., millimeters). Method 200 may further include determining pathology characteristics in the extracted cardiovascular geometry being targeted for treatment (step 206). For example, step 206 may include indicating the presence or absence of plaque at one or more locations. If plaque exists, a list of one or more measurements of coronary plaque composition, burden and location may be obtained or generated. Method 200 may further include defining an objective function for one or more devices and delivery systems (step 208), such as based on design considerations (e.g., shape, fracture resistance, drug distribution) and a list of one or more estimates of biophysical hemodynamic and mechanical characteristics, such as tissue stress, vessel injury, drug delivery, uniformity of drug distribution, wall-shear stress, oscillatory shear index, particle residence time, Reynolds number, Womersley number, local flow rate, and turbulent kinetic energy. Method 200 may further include optimizing devices and delivery systems for the defined objective function (step 210), such as by optimizing specifications of devices and delivery systems based on the objective functions, and/or perturbing geometry by virtually deployed devices from existing designs or using a new design for computational fluid dynamics or structural mechanics analysis to evaluate the objective function. Method 200 may further include optimizing devices and delivery systems for the defined objective function (step 210), such as by inputting device and/or delivery system variables into an optimization algorithm to optimize the device's and/or delivery system's characteristics. Method 200 may further include recommending a device and/or delivery system from an inventory or catalog, or making a personalized or customized device and/or delivery system, such as using 3D printing (step 212). For example, step 212 may include choosing an optimal device design from inventory (e.g., a device catalog consistent with FIG. 2) using patient-specific geometry and evaluation scores, or determining specifications for a customized device and delivery mechanism (e.g., custom order, 3D printing, etc.). Method 200 may further include storing the inventory selection or specification in an electronic storage medium (e.g., hard drive, computer RAM, network communication channel), and/or transmitting the selected device design to a physician, such as over a network.

Method 200 will now be described in more detail below with reference to FIG. 2 and specific exemplary characteristics and exemplary steps. In one embodiment, step 202 may include obtaining image and patient information by acquiring a digital representation (e.g., the memory or digital storage [e.g., hard drive, network drive] of a computational device such as a computer, laptop, DSP, server, etc.) of a patient's heart scan and the following estimates of physiological or phenotypic parameters of the patient, including:

Patient age, gender, height, and weight;
Heart rate;
Systolic and diastolic blood pressure;
Blood properties including: plasma, red blood cells (erythrocytes), hematocrit, white blood cells (leukocytes) and platelets (thrombocytes), viscosity, yield stress, etc.;
Cardiac function (ejection fraction); and
Epicardial fat volume.

In one embodiment, step 204 may include generating a patient specific model of geometry for one or more of blood vessels, myocardium, aorta, valves, plaques, and chambers. This geometry may be represented as a list of points in space (possibly with a list of neighbors for each point) in which the space can be mapped to spatial units between points (e.g., millimeters). In one embodiment, the patient-specific model may include the geometry for the patient's ascending aorta, coronary artery tree, myocardium, valves, and/or chambers. This geometry may be represented as a list of points in space (possibly with a list of neighbors for each point) in which the space can be mapped to spatial units between points (e.g., millimeters). This model may be derived by performing a cardiac CT imaging of the patient in the end diastole phase of the cardiac cycle. This image then may be segmented manually or automatically to identify voxels belonging to the aorta and the lumen of the coronary arteries. Given a 3D image of coronary vasculature, many methods exist in the literature for extracting a patient-specific model of cardiovascular geometry. For example, in one embodiment, server systems 106 may generate a three-dimensional solid model and/or three-dimensional mesh based on the received patient-specific anatomical data. For example, server systems 106 may generate the three-dimensional model and/or mesh based on any of the techniques described in U.S. Pat. No. 8,315,812 by Taylor et al., which issued on Nov. 20, 2012, the entirety of which is hereby incorporated herein by reference. Inaccuracies in the geometry extracted automatically may be corrected by a human observer who compares the extracted geometry with the images and makes corrections as needed. Once the voxels are identified, the geometric model can be derived (e.g., using marching cubes).

For the location targeted for treatment, step 204 may further include obtaining geometric quantities of coronary arteries from the patient-specific geometric model, such as, for example, characteristics of the coronary cross-sectional area, the surface of coronary geometry, the coronary centerline, and coronary deformation. Characteristics of the coronary cross-sectional area include, for example, the cross-sectional lumen area along the coronary centerline, such as the degree of tapering, and any irregularity (or circularity) of the cross-sectional lumen boundary. The degree of tapering may be obtained, for instance, by acquiring sample centerline points in a certain interval (e.g., twice the diameter of the vessel) and computing a slope of the linearly-fitted cross-sectional area.

Other characteristics of the coronary cross-sectional area include, for example, the location, length, and degree of stenotic lesions. The location of stenotic lesions may be obtained, for example, by detecting minima of the cross-sectional area curve. The minima are detected via detecting locations where the first derivative of the area curve is zero and the second derivative is positive. The cross-sectional area profile should be smoothed to avoid detecting artificial peaks. The length of stenotic lesions may be obtained, for example, by computing the proximal and distal locations from the stenotic lesion where the cross-sectional area is recovered. Finally, the degree of stenotic lesions may be evaluated, for example, based on reference values of a smoothed cross-sectional area profile using Fourier smoothing or kernel regression.

Characteristics of the surface of coronary geometry may include, for example, a three-dimensional surface curvature of geometry, including, for instance, Gaussian function, maximum, minimum, and mean.

Characteristics of the coronary centerline include, for example, the curvature (bending) and tortuosity (non-planarity) of the coronary centerline. The curvature may be obtained, for example, by computing Frenet curvature using the following equation:

$$\kappa = \frac{|p' \times p''|}{|p'|^3},$$

where p is a coordinate of the centerline,
or by computing an inverse of the radius of a circumscribed circle along the centerline points. The tortuosity may be obtained, for example, by computing Frenet torsion using the following equation:

$$\tau = \frac{(p' \times p'') \cdot p'''}{|p' \times p''|^2},$$

where p is a coordinate of the centerline.

Characteristics of coronary deformation may include, for example, distensibility of the coronary artery over a cardiac cycle, the bifurcation angle change over a cardiac cycle, and the curvature change over a cardiac cycle. This metric, therefore, may require multi-phase CCTA (e.g., diastole and systole).

In one embodiment, step 206 may include determining pathology characteristics in the extracted cardiovascular geometry being targeted for treatment, by indicating the presence or absence of plaque at one or more locations. If plaque exists, a list of one or more measurements of coronary plaque composition, burden and location may be generated or obtained. For the location targeted for treatment, step 206 may include obtaining quantities of coronary pathology from the patient-specific geometric model, including, for example, plaque burden (volume) and type, such as the intensity of plaque, and adverse plaque characteristics of existing plaque, such as the presence of positive remodeling, the presence of low attenuation plaque, and the presence of spotty calcification.

In one embodiment, step 208 may include defining the objective function for device and delivery system by (a) defining the design variables for optimization; (b) defining metrics based on design consideration and a list of one or more estimates of biophysical hemodynamic and mechanical characteristics; and (c) defining the objective function based on defined metrics with weights.

Non-limiting examples of design variables for optimization include, for instance, the type of stent (e.g., coil, tube, slotted, etc.), stent length, symmetry, materials, percentage metal coverage, surface finish, tapering/contour/cross-section, strut geometry, and drug content and dose (amount and release rate). Strut geometry may include, for example, shape, thickness, spacing, and number of struts.

Non-limiting examples of metrics based on design consideration and a list of one or more estimates of biophysical hemodynamic and mechanical characteristics include, for example, metrics for device optimization and metrics for delivery system optimization. Metrics for device optimization may include, for example, characteristics of hemodynamics and mechanics derived from computational flow dynamics, such as flow mechanics characteristics, solid mechanics characteristics, and clinical event characteristics.

Non-limiting examples of flow mechanics characteristics include, for example, mean wall-shear stress, oscillatory shear index (OSI), particle residence time, turbulent kinetic energy (TKE), drug delivery, and uniformity of drug distribution. Mean wall-shear stress is defined as $$\left| \frac{1}{T_1 - T_0} \int_{T_0}^{T_1} \vec{t}_s \, dt \right|,$$

wherein $\vec{t}_s$ is the wall shear stress vector defined as the in-plane component of the surface traction vector. OSI is defined as $$\frac{1}{2}\left(1 - \frac{\left|\frac{1}{T_1-T_0}\int_{T_0}^{T_1} \vec{t}_s \, dt\right|}{\frac{1}{T_1-T_0}\int_{T_0}^{T_1} |\vec{t}_s| \, dt}\right),$$

and is a measure of the uni-directionality of shear stress. Particle residence time, in turn, is a measure of the time it takes blood to be flushed from a specified fluid domain. Finally, TKE is a measure of the intensity of turbulence associated with eddies in turbulent flow, and is characterized by measured root-mean-square velocity fluctuation. TKE can be normalized by kinetic energy.

Non-limiting examples of solid mechanics characteristics include, for example, tissue stresses, fracture resistance, flexibility, and deliverability. Non-limiting examples of clinical event characteristics include, for instance, vessel injury, risk of embolization (covered stents), risk of restenosis or thrombosis/coagulation, and side branch impairment.

As noted above, the characteristics of hemodynamics and mechanics are derived from computational flow dynamics. Computer methods to simulate blood flow and structural mechanics have been well-studied, and the simulation may be accomplished with known techniques. For example, to obtain transient characteristics of blood flow, pulsatile flow simulation may be performed by using a lumped parameter coronary vascular model for downstream vasculatures, inflow boundary condition with coupling a lumped parameter heart model, and a closed loop model to describe the intramyocardial pressure variation resulting from the interactions between the heart and arterial system during the cardiac cycle.

Metrics for delivery system optimization may include, for example, length, flexibility/functionality, pre-shaped guidewire for ordering size/length/composition, balloon pressure, and balloon compliance.

Regarding defining the objective function based on defined metrics with weights, weights for each metric may be determined on the basis of intended design consideration. Non-limiting examples of intended design consideration include performance, deliverability, and durability.

In one embodiment, step 210 may include optimizing device and delivery system for the defined objective function by evaluating an existing design from an inventory or catalog and a new design. The evaluations may involve, for example, perturbing the geometry of the virtually deployed devices to perform a computational fluid dynamics or structural mechanics analysis in order to evaluate their objective function.

In one embodiment, step 212 may include recommending a personalized or customized device or delivery system from an inventory or catalog, or manufacturing the personalized or customized device or delivery system using 3D printing. This can be achieved by (a) saving the patient specific geometry, the results of the evaluation score, and device designs as a digital representation (e.g., the memory or digital storage [e.g., hard drive, network drive] of a computational device such as a computer, laptop, DSP, server, etc.); (b) making a recommendation from the inventory or catalog, and (c) customizing the design to the patient.

Making the recommendation may include, for example, providing a digital representation of patient-specific geometry with a recommendation of the optimal design for the customer so that the customer may select devices from an inventory, such as an existing hospital inventory, or a device catalog. In one embodiment, the device or delivery system that has the highest evaluation score is chosen. In another embodiment, the device or delivery system that has the most similar characteristics to the design with the highest evaluation score is chosen.

Customizing the design to the patient may include, for example, providing a digital representation of patient-specific geometry with a recommendation of an optimal design for the customer for manufacturing a new design of device and delivery system. The resulting customized design may be ordered for 3D printing based on the optimal design specification, which is defined as design variables. Non-limiting examples of these design variables include, for example, type of stent (e.g., coil, tube, slotted, etc.), length, symmetry, materials, percentage metal coverage, surface finish, tapering/contour/cross-section, and strut geometry, such as shape, thickness, spacing, number of struts, and drug content and dose (amount and release rate). Finally, the output model may be saved to an electronic storage medium (e.g., hard disk, computer RAM, network drive, etc.).

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed:

1. A computer-implemented method of identifying a personalized cardiovascular device based on patient-specific geometrical information, the method comprising:
   generating or obtaining a patient specific model of at least a portion of a patient's vasculature from image data of the patient's vasculature and one or more measured or estimated physiological or phenotypic parameters of the patient;
   determining one or more pathology characteristics of the patient from the patient specific model;
   defining one or more variables of a personalized cardiovascular device designed to treat the one or more pathology characteristics of the patient;
   defining an objective function defined by the one or more variables and one or more estimates of hemodynamic or mechanical characteristics derived from simulating the personalized cardiovascular device being deployed in the patient specific model;
   optimizing the objective function, by iteratively simulating at least one change in the one or more variables using fluid dynamic or structural mechanic analyses of one or more iterative updates of the personalized cardiovascular device being deployed in the patient specific model, to identify the one or more variables that optimize the one or more estimates of hemodynamic or mechanical characteristics in the patient specific model; and
   using the identified one or more variables to either (i) select a device from a set of available devices or (ii) manufacture a desired personalized cardiovascular device.

2. The method of claim 1, wherein the personalized cardiovascular device comprises at least one of an implantable device and a device for delivery of an implantable device.

3. The method of claim 1, wherein generating the patient specific model includes acquiring one or more measured or estimated physiological or phenotypic parameters of the patient chosen from patient age, gender, height, weight, heart rate, systolic and diastolic blood pressure, blood properties, cardiac function, and epicardial fat volume.

4. The method of claim 3, wherein the blood properties are chosen from at least one of plasma, red blood cells, hematocrit, white blood cells, platelets, viscosity and yield stress.

5. The method according to claim 3, wherein the one or more measured or estimated physiological or phenotypic parameters of the patient are measured.

6. The method according to claim 3, wherein the one or more measured or estimated physiological or phenotypic parameters of the patient are estimated.

7. The method of claim 1, wherein determining one or more pathology characteristics from the patient specific model includes determining at least one of plaque composition, burden, and location.

8. The method of claim 1, wherein determining one or more pathology characteristics from the patient specific model includes determining adverse characteristics of existing plaque chosen from at least one of a presence of positive remodeling, a presence of low attenuation plaque, and a presence of spotty calcification.

9. The method of claim 1, wherein the one or more variables of the personalized cardiovascular device are chosen from at least one of device shape, fracture resistance, and drug distribution.

10. The method of claim 1, wherein the hemodynamic or mechanical characteristics are chosen from tissue stress, vessel injury, drug delivery, uniformity of drug distribution, wall-sheer stress, oscillatory shear index, particle residence time, Reynolds number, Womersley number, local flow rate, and turbulent kinetic energy.

11. The method of claim 1, wherein the personalized cardiovascular device is selected from the set of available devices in an inventory or a catalog.

12. The method according to claim 11, further comprising storing the personalized cardiovascular device selected from the inventory or the catalog in an electronic storage medium.

13. The method according to claim 11, further comprising transmitting the personalized cardiovascular device selected from the inventory or the catalog to a physician.

14. The method of claim 1, wherein the personalized cardiovascular device is manufactured using 3D printing.

15. The method according to claim 14, further comprising storing a specification of the personalized cardiovascular device manufactured using 3D printing in an electronic storage medium.

16. The method according to claim 14, further comprising transmitting a specification of the personalized cardiovascular device manufactured using 3D printing to a physician.

17. A system for identifying a personalized cardiovascular device based on patient-specific geometrical information, the system comprising:
   a data storage device storing instructions for identifying a personalized cardiovascular device based on patient-specific geometrical information; and
   a processor configured to execute the instructions to perform a method including the steps of:
      generating or obtaining a patient specific model of at least a portion of a patient's vasculature from image data of the patient's vasculature and one or more measured or estimated physiological or phenotypic parameters of the patient;

determining one or more pathology characteristics of the patient from the patient specific model;

defining one or more variables of a personalized cardiovascular device designed to treat the one or more pathology characteristics of the patient;

defining an objective function defined by the one or more variables and one or more estimates of hemodynamic or mechanical characteristics derived from simulating the personalized cardiovascular device being deployed in the patient specific model;

optimizing the objective function, by iteratively simulating at least one change in the one or more variables using fluid dynamic or structural mechanic analyses of one or more iterative updates of the personalized cardiovascular device being deployed in the patient specific model, to identify one or more variables that optimize the one or more estimates of hemodynamic or mechanical characteristics in the patient specific model; and using the identified one or more variables to either (i) select a device from a set of available devices or (ii) manufacture a desired personalized cardiovascular device.

18. The system of claim 17, wherein the personalized cardiovascular device comprises at least one of an implantable device and a device for delivery of an implantable device.

19. A non-transitory computer readable medium for use on at least a computer system containing computer-executable programming instructions for identifying a personalized cardiovascular device based on patient-specific geometrical information, the instructions being executable by the computer system for:

generating, at the computer system, a patient specific model of at least a portion of the patient's vasculature and one or more measured or estimated physiological or phenotypic parameters of the patient;

determining one or more pathology characteristics of the patient from the patient specific model;

defining one or more variables of a personalized cardiovascular device designed to treat the one or more pathology characteristics of the patient;

defining an objective function defined by the one or more variables and one or more estimates of hemodynamic or mechanical characteristics derived from simulating the personalized cardiovascular device being deployed in the patient specific model;

optimizing the objective function, by iteratively simulating at least one change in the one or more variables using fluid dynamic or structural mechanic analyses of one or more iterative updates of the personalized cardiovascular device being deployed in the patient specific model, to identify one or more variables that optimize the one or more estimates of hemodynamic or mechanical characteristics of the patient specific model; and using the identified one or more variables to either (i) select a device from a set of available devices or (ii) manufacture a desired personalized cardiovascular device.

20. The non-transitory computer readable medium of claim 19, wherein the personalized cardiovascular device comprises at least one of an implantable device and a device for delivery of an implantable device.

* * * * *